(12) United States Patent
Yoneda et al.

(10) Patent No.: US 6,667,328 B2
(45) Date of Patent: Dec. 23, 2003

(54) THERAPEUTIC AGENTS FOR DIABETES

(75) Inventors: Fumio Yoneda, Osaka (JP); Shizuko Muraoka, Osaka (JP); Hironori Ohde, Osaka (JP); Mayumi Watanabe, Osaka (JP); Kazunori Urabe, Osaka (JP); Ikuko Tochikawa, Osaka (JP)

(73) Assignee: Fujimoto Brothers Co., Ltd., Osaka (JP)

( * ) Notice: Subject to any disclaimer, the term of this patent is extended or adjusted under 35 U.S.C. 154(b) by 0 days.

(21) Appl. No.: 09/914,921

(22) PCT Filed: Jan. 22, 2001

(86) PCT No.: PCT/JP01/00398
§ 371 (c)(1),
(2), (4) Date: Sep. 26, 2001

(87) PCT Pub. No.: WO01/52849
PCT Pub. Date: Jul. 26, 2001

(65) Prior Publication Data
US 2003/0078193 A1 Apr. 24, 2003

(30) Foreign Application Priority Data
Jan. 24, 2000 (JP) ........................................ 2000-014970

(51) Int. Cl.[7] .............................................. A61K 31/425
(52) U.S. Cl. ........................ 514/365; 514/369; 514/866
(58) Field of Search ................................ 514/365, 369, 514/866

(56) References Cited

U.S. PATENT DOCUMENTS

| | | | | |
|---|---|---|---|---|
| 5,143,929 A | * | 9/1992 | Belliott et al. | ............... 514/366 |
| 5,750,712 A | * | 5/1998 | Yoneda et al. | ............... 548/186 |
| 6,380,229 B1 | * | 4/2002 | Yoneda et al. | ............... 514/369 |

FOREIGN PATENT DOCUMENTS

| | | |
|---|---|---|
| EP | 0 332 332 | 9/1989 |
| EP | 0 697 410 | 2/1996 |
| EP | 697410 | 2/1996 |
| EP | 1 142 885 | 10/2001 |
| JP | 7-165371 | 6/1995 |
| JP | 8-92249 | 4/1996 |
| JP | 8-157461 | 6/1996 |
| JP | 09110845 | * 4/1997 |
| JP | 7-165371 | 6/1997 |
| JP | 9-165371 | 6/1997 |
| JP | 2000-26438 | 1/2000 |

OTHER PUBLICATIONS

Randall W. Whitcomb et al., "Thiazolidinediones", Expert Opinion on Investigation Drugs, Ashley Publications, Ltd., Vol. 4, No. 12, Dec. 1, 1995, pp. 1299–1309.

* cited by examiner

Primary Examiner—Kevin E. Weddington
(74) Attorney, Agent, or Firm—Wenderoth, Lind & Ponack, L.L.P.

(57) ABSTRACT

This invention relates to therapeutic agents for diabetes comprising a 2-(N-cyanoimino)thiazolidine-4-one derivatives represented by formula I or a solvate or a pharmaceutically acceptable salt thereof as an active ingredient:

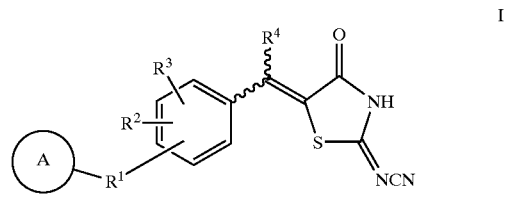

wherein ring A represents a benzene ring, a condensed ring, or a heterocyclic ring, each of which may be substituted by one or more substituents selected from a straight or branched $C_1$–$C_4$ alkyl group, a haloalkyl group, a halogen atom or —$OR^5$, $R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—, $R^2$ and $R^3$ are the same or different and each represents a hydrogen atom, a $C_1$–$C_4$ alkyl group, —$OR^8$ or a halogen atom, $R^4$ represents a hydrogen atom or a $C_1$–$C_4$ alkyl group, $R^5$ represents a hydrogen atom or a $C_1$–$C_4$ alkyl group, $R^6$ represents a straight or branched $C_1$–$C_4$ alkylene or alkenylene group, $R^7$ represents a hydrogen atom or a $C_1$–$C_4$ alkyl group, $R^8$ represents a hydrogen atom, a $C_1$–$C_4$ alkyl group or an aralkyl group, X represents an oxygen atom or a sulfur atom, the configuration of the exocyclic methylene group at 5-position of the thiazolidine ring includes both E- and Z-configuration.

18 Claims, No Drawings

THERAPEUTIC AGENTS FOR DIABETES

This application is a 371 of PCT/JP01/00398 filed Jan. 22, 2001.

BACKGROUND OF THE INVENTION

1. Field of the Invention

The present invention provides therapeutic agents for diabetes comprising a 2-(N-cyanoimino)thiazolidin-4-one derivative or a solvate or a pharmaceutically acceptable salt thereof as an active ingredient.

2. Description of the Related Art

Diabetes, recently mentioned as a representative example of life-style related diseases, is a disease that shows an acute symptom due to the remarkably high blood sugar or ketoacidosis, or various chronic, general metabolic abnormalities arising from a prolonged high blood sugar status or a decrease in glucose tolerance. The crisis of the diabetes has congenital genetic factors and acquired environmental factors such as eating habits and exercise levels. Both of them are mutually influenced, thus resulting in various types of diabetic crisis and various types of disease progress.

The pathogenic causes are insulin productive disorders, secretion disorders or reductions in activities and sensitivities of the secreted insulin. The diabetes is largely grouped into the following two types: insulin-dependent diabetes mellitus (also known as Type 1 diabetes) and non-insulin-dependent diabetes mellitus (also known as Type 2 diabetes). It is the latter insulin-nondependent diabetes a trend of which is a remarkable increase in a number of patients, and furthermore has a lot of diabetes.

The hyperlipidemia is mentioned as one of the life-style-related diseases as much as so for diabetes. The hyperlipidemia means status in which levels of lipids in plasma are increased over normal ranges. The lipids in the plasma are triglycerides, cholesterol, phospholipids, and free fatty acids. All conditions in which any one type of these lipids or multiple types have increased are designated as hyperlipidemia. Almost all lipids in the blood exist as lipoproteins combined with proteins. The free fatty acids in the blood are combined with albumin or lipoproteins; these complexes are also included in the concept of the lipoproteins in the present invention.

Diabetes has been recognized since ancient times, and diagnostic and therapeutic methods have been investigated for many years. As the oral hypoglycemic agents, sulfonylureas (for example, tolbutamide, chlorpropamide and glibenclamide), biguanides (for example, metformin and buformin) and α-glucosidase inhibitors (for example, acarbose and voglibose) can be listed. In addition, recently the agents for insulin-resistance amelioration (for example, troglitazone, rosiglitazone and pioglitazone) have been developed and marketed. Thus, currently there are various types of therapeutic agents, however, still the patient number has been continuously increasing. Thus, the development of more efficient agents is anticipated.

Currently targets of diabetes therapies and controls are said to inhibit pathogenesis and progress of vascular complications that lead to serious problems, and to allow the diabetes patients have longevity and curability equivalent to normal subjects. Many diabetes patients tend to develop microangiopathy and macroangiopathy that are frequently associated with hypertriglyceridemia and hypercholesterolemia, risk factors of complications. However, because of pathogenic differences between diabetes, hypertriglyceridemia and hypercholesterolemia, different agents have been applied for the respective therapies.

For example, as a first choice for hypertriglyceridemia, dextran sulflate sodium, nicotinic acid derivatives or fibrates have been selected, and among them, bezafibrate has been well known. For hypercholesterolemia, HMG-CoA reductase inhibitors, referred as statins, such as pravastatin and simvastatin have been widely in clinical usage. Generally, when only a cholesterol level is high, HMG-CoA reductase inhibitors are used. However, the combined administration of HMG-CoA reductase inhibitors with fibrates or nicotinic acids gives rise to an increased risk of rhabdomyolysis.

It has been already known that dioxothiazolidine derivatives act for lowering blood sugar to some degree. 5-(Benzyl)thiazolidine-2,4-dione, reported 1971 by Taylor et al; AL-321 (Chemical name: 5-[4-(2-methyl-2-phenypropoxy)benzyl]thiazolidine-2,4-dione, Chem. Pharm. Bull., 30, 3580 (1980)) reported 1982 by Sohda et al; ciglitazone, which obtained as a result of a optimization of AL-321; troglitazone, rosiglitazone, and pioglitazone, which are chosen for clinical development from a large number of thiazolidine derivatives synthesized in many enterprises through design and structure-activity relationship analysis of ciglitazone analogue; for example. Any of AL-321, ciglitazone, troglitazone, rosiglitazone and pioglitazone has a 5-(benzyl)thiazolidine-2,4-dione moiety, a common structural unit. And recently troglitazone, rosiglitazone and pioglitazone were marketed as antidiabetic agents.

However, within a few months after troglitazone on market, adverse effects of severe hepatic symptoms, including death cases, were reported, thereby, monotherapy with this agent was considered to generate a high risk rather than antidiabetic effects. Thus, combined administration of three agents; troglitazone, sulfonylureas and biguanides, has been regarded desirable. When rosiglitazone or pioglitazone is administered, periodical blood tests to monitor liver function are required similar to the case of troglitazone. Developments of antidiabetic agents more excellent in efficacy and safety have been anticipated.

SUMMARY OF THE INVENTION

In Japanese Patent Application No. 1998-232216, the present inventor shows that novel 2-(N-cyanoimino) thiazolidin-4-one derivatives possess activities to improvement of the hyperlipidemia such as hypertriglyceridemia and hypercholesterolemia. By conducting intensive research, 2-(N-cyanoimino)thiazolidin-4-one derivatives were found to have blood sugar lowering effects as much as troglitazone in diabetes model animals, despite its structural difference from 5-(benzyl)thiazolidine-2,4-dione, the structure of which has been regarded desirable. Thus the present invention was successfully established.

In summary, the compounds of the present invention act for improving hyperlipidemia as well as diabetes, and these traits prevent from the two big risk factors of vascular disease, diabetes and hyperlipidemia simultaneously. This means that said compounds act synergically from both aspects of the diabetes and hyperlipidemia, for improvement in complications such as microangiopathy and macroangiopathy. The said compounds can be excellent therapeutic agents for diabetes extremely suit aims of the diabetes control and therapy "prevention of pathogenesis and progression of vascular complications that evoke serious states".

This invention provides therapeutic agents for diabetes comprising a 2-(N-cyanoimino)thiazolidine-4-one derivative represented by formula I or a solvate or a pharmaceutically acceptable salt thereof as an active ingredient.

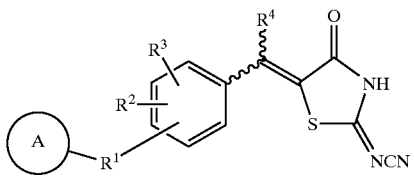

wherein ring A represents a benzene ring, a condensed ring or a heterocyclic ring, each of which may be substituted by one or more substituents selected from a straight or branched $C_1$–$C_4$ alkyl group, a haloalkyl group, a halogen atom or —$OR^5$;

$R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—;

$R^2$ and $R^3$ are the same or different and each represents a hydrogen atom, a $C_1$–$C_4$ alkyl group, —$OR^8$ or a halogen atom;

$R^4$ represents a hydrogen atom or a $C_1$–$C_4$ alkyl group, $R^5$ represents a hydrogen atom or a $C_1$–$C_4$ alkyl group;

$R^6$ represents a straight or branched $C_1$–$C_4$ alkylene or alkenylene group;

$R^7$ represents a hydrogen atom or a $C_1$–$C_4$ alkyl group;

$R^8$ represents a hydrogen atom, a $C_1$–$C_4$ alkyl group or an aralkyl group;

X represents an oxygen atom or a sulfur atom;

the configuration of the exocyclic methylene group at 5-position of the thiazolidine ring includes both E- and Z-configuration.

The term therapeutic agents for diabetes of the present invention means the agents administered to diabetes-prone subjects, that is, prophylactic agents as well as the agents for treatment of diabetes patients.

"Salts" refers to low toxic salts derived from sodium, potassium, ammonia or organic amines, for instance.

"$C_1$–$C_4$ alkyl group" refers to methyl, ethyl, n-propyl, iso-propyl, n-butyl or tert-butyl, for instance.

"$C_1$–$C_4$ alkoxy group" refers to methoxy, ethoxy, n-propoxy, iso-propoxy, n-butoxy or tert-butoxy, for instance.

"halogen atom" refers to generally fluorine atom, chlorine atom, bromine atom, or iodine atom. More preferably it is fluorine atom or chlorine atom.

"ring A" refers to a benzene ring, a benzodioxole ring, a benzofuran ring, a benzothiazole, a fluorene ring, an indan ring, an indoline ring or a pyridine ring, connecting with $R^1$ at any position, for instance.

The compounds of the present invention can be obtained in accordance with the method described in Japanese Patent Application No. 1998-232216, for instance. There are geometric isomers for these compounds, however, in solution, reversible isomerization of the exocyclic methylene group at 5-position of the thiazolidine ring occurs very easily by the action of light or heat.

DESCRIPTION OF THE PREFERRED EMBODIMENTS

Particularly preferred compounds represented by formula I are as follows;

2-(N-Cyanoimino)-5-[(E)-4-styrylbenzylidene]thiazolidin-4-one;
2-(N-Cyanoimino)-5-[(E)-4-(α-methylstyryl)benzylidene]thiazolidin-4-one;
2-(N-Cyanoimino)-5-[4-(benzyloxymethyl)benzylidene]thiazolidin-4-one;
2-(N-Cyanoimino)-5-[(E)-4-(β-methylstyryl)benzylidene]thiazolidin-4-one;
2-(N-Cyanoimino)-5-[4-(3-phenylpropoxy)benzylidene]thiazolidin-4-one;
2-(N-Cyanoimino)-5-[4-(4-chlorophenoxy)benzylidene]thiazolidine-4-one;
2-(N-Cyanoimino)-5-(4-phenylthiobenzylidene)thiazolidin-4-one;
2-(N-Cyanoimino)-5-[(E)-4-(2-fluorostyryl)benzylidene]thiazolidin-4-one;
2-(N-Cyanoimino)-5-[4-(2,5-dimethylphenoxy)benzylidene]thiazolidin-4-one;
2-(N-Cyanoimino)-5-(4-phenethyloxybenzylidene)thiazolidin-4-one;
2-(N-Cyanoimino)-5-[4-(2-phenylpropoxy)benzylidene]thiazolidin-4-one;
2-(N-Cyanoimino)-5-(3-phenethyloxybenzylidene)thiazolidin-4-one;
2-(N-Cyanoimino)-5-[4-(benzyloxybenzylidene)thiazolidin-4-one;
2-(N-Cyanoimino)-5-[4-(5-chlorobenzofuran-2-yl)benzylidene]thiazolidin-4-one;
2-(N-Cyanoimino)-5-[(E)-4-(4-methoxystyryl)benzylidene]thiazolidin-4-one;
2-(N-Cyanoimino)-5-(3-phenoxybenzylidene)thiazolidin-4-one;
2-(N-Cyanoimino)-5-[4-(1,3-benzodioxole-5-ylmethoxy)benzylidene]thiazolidin-4-one;
2-(N-Cyanoimino)-5-[4-(4-methylbenzyloxy)benzylidene]thiazolidin-4-one,
2-(N-Cyanoimino)-5-[4-(4-chlorobenzyloxy)benzylidene]thiazolidin-4-one;
2-(N-Cyanoimino)-5-[3-methoxy-(E)-4-styrylbenzylidene]thiazolidin-4-one;
2-(N-Cyanoimino)-5-(2-phenethyloxybenzylidene)thiazolidin-4-one;
2-(N-Cyanoimino)-5-(4-phenoxybenzylidene)thiazolidin-4-one;
2-(N-Cyanoimino)-5-[3-(benzyloxy)benzylidene]thiazolidin-4-one;
2-(N-Cyanoimino)-5-[4-(benzylthio)benzylidene]thiazolidin-4-one;
2-(N-Cyanoimino)-5-(4-phenethylbenzylidene)thiazolidin-4-one;
2-(N-Cyanoimino)-5-[4-[2-(4-chlorophenyl)ethoxy]benzylidene]thiazolidin-4-one;
2-(N-Cyanoimino)-5-[1-[(E)-4-(4-methoxystyryl)phenyl]ethylidene]thiazolidin-4-one;
2-(N-Cyanoimino)-5-(4-benzyloxy-2,5-dimethylbenzylidene)thiazolidin-4-one;
2-(N-Cyanoimino)-5-[(E)-3-styrylbenzylidene]thiazolidin-4-one.

The compounds of the present invention and pharmaceutically acceptable salts thereof can be orally or parenterally administered either alone or generally in the form of appropriate pharmaceutical compositions such as tablets, powders, granules, capsules, syrups, or injections comprised of pharmaceutically acceptable carriers, diluents, solubilizers, or other pharmaceutical additives. Oral administration is preferred. Among these preparations, oral administration preparations are particularly preferable.

The dosage will depend on the condition, age, body weight, and other factors of each patient or efficacy of an active ingredient. Generally, when the compound of the present invention is orally administered, the daily dose of the present invention preferably ranges from 10 to 2000 mg, more preferably from 100 to 1000 mg for adult, and is administered once or in several divided doses a day.

EXAMPLE 1

2-(N-Cyanoimino)-5-[(E)-4-stylylbenzylidene]thiazolidin-4-one (Compound 1)

A mixture of 4.48 g (0.025 mol) of 2-(N-cyanoimino)thiazolidin-4-one potassium salt, 5.47 g (0.026 mol) of trans-4-stilbencarboxaldehyde and 2.02 g (0.026 mol) of ammonium acetate in 100 mL of ethanol was heated for 2 hours under reflux. After cooling, ether was added to the reaction mixture and the precipitated potassium salt of the title compound was collected by filtration. To the rapidly stirring suspension of the salt in 50 mL of acetone, 5 mL of conc. hydrochloric acid was added dropwise and then 250 mL of water was added. The precipitate was collected and dried under reduced pressure to yield the title compound as yellow crystals. The yield was 88% (7.32 g, 0.022 mol).

mp: >265° C. (dec.) (ethanol-DMF)

EI-MS: 331(M+), 236, 202, 179

IR (KBr, cm$^{-1}$): 3015, 2920, 2740, 2185, 1725, 1580, 1505, 1490, 1340, 1290, 1170, 580, 540, 500

$^1$H NMR (DMSO-d6, ppm): δ=5.80–7.00 (1H, br), 7.20–8.10 (11H, m), 7.86 (1H, s)

Elemental analysis for $C_{19}H_{13}N_3OS$ (331.399): Calcd.: H, 3.95; C, 68.86; N, 12.68(%); Found: H, 4.15; C, 68.94; N, 12.40(%)

In the same manner, the compounds 2 to 61 shown in Table 1 to 6 were prepared. Their structural formulas, yields, and physical properties are shown in Table 1 to 6. R and R' used in these tables represent R and R' in the formula II respectively.

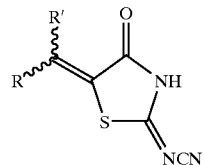

II

| Abbreviations used and notes in Table 1 to 6 are as follows: | |
|---|---|
| Ex. | Example |
| mp | melting point |
| recryst solv | recrystallization solvent |
| EI-MS | electron impact ionization mass spectroscopy |
| IR | infrared spectroscopy |
| EA | elemental analysis |
| $^1$H NMR | proton nuclear magnetic resonance spectra |
| s | singlet |
| d | doublet |
| dd | doublet of doublets |
| t | triplet |
| m | multiplet |
| br | broad |
| J | coupling constant |

*1: After heating for 10 minutes at 130° C. without solvent, the soluble part of reaction mixture in chloroform is chromatographed on a silica gel column.
*2: n-Butanol was used as solvent.
*3: E = ethanol, DMF = N,N-dimethylformamide, I = isopropanol, A = acetone, M = methanol, EA = ethyl acetate, H = hexane
*4: Solvent; 10% Pyridine-d5/DMSO-d6

TABLE 1

| Ex No. | Description | Yield (%) | R | R' | mp (°C) (recryst solv*3) | EI-MS (m/z) | IR (KBr, cm⁻¹) | ¹H-NMR (DMSO-d6, δ: ppm) | Molecular formula (Molecular weight) | EA(%) Calcd./Found |
|---|---|---|---|---|---|---|---|---|---|---|
| 1 | yellow crystals | 88 | (4-methylphenyl)-CH=CH-phenyl | H | 265 (dec) (E/DMF) | 331(M⁺), 236, 202, 179 | 3015, 2920, 2740, 2185, 1725, 1580, 1505, 1490, 1340, 1290, 1170, 580, 540, 500 | 5.80–7.00(1H, br), 7.20–8.10(11H, m), 7.86(1H, s) | $C_{19}H_{13}N_3OS$ (331.399) | H 3.95, C 68.86, N 12.68 / H 4.15, C 68.94, N 12.40 |
| 2 | orange-yellow crystals | 84 | (4-methylphenyl)-C(CH3)=CH-phenyl | H | 226–277.5 (E/DMF) | 345(M⁺), 258, 243, 162 | 3150, 3080, 2925, 2210, 1724, 1580, 1360, 1348, 1180, 742, 700, 588, 525 | 2.27(3H, br), 3.50–4.40(1H, br), 7.08(1H, br), 7.20–7.55(5H, m), 7.60–7.80(4H, m), 7.88(1H, s) | $C_{20}H_{15}N_3OS$ (345.426) | H 4.38, C 69.54, N 12.16 / H 4.59, C 69.51, N 11.99 |
| 3 | pale yellow crystals | 90 | (4-methylphenyl)-CH2-O-CH2-phenyl | H | 170.5–171.5 (E/DMF) | 349(M⁺), 320, 258, 243, 230, 162, 147, 135, 115, 103, 91, 79, 77 | 3200, 3110, 2200, 1740, 1600, 1350, 1307, 1250, 1200, 1190, 1146, 830, 755, 562, 540 | 3.86(1H, br), 4.57(2H, s), 4.62(2H, s), 7.37(5H, s), 7.60(4H, s), 7.87(1H, s) | $C_{19}H_{15}N_3O_2S$ (349.414) | H 4.33, C 65.31, N 12.03 / H 4.64, C 65.54, N 11.70 |
| 4 | yellow needles | 66 | (4-methylphenyl)-C(=CH-phenyl)-CH3 | H | 236.5–237.5 (E/DMF) | 345(M⁺), 320, 249, 233, 205 | 2950, 2200, 1717, 1598, 1360, 1293, 1248, 1202, 1181, 763, 721, 700, 582, 542, 520 | 2.28(3H, s), 6.05(1H, br), 6.81(1H, s), 7.20–7.80(9H, m), 7.84(1H, s) | $C_{20}H_{15}N_3OS$ (345.426) | H 4.38, C 69.54, N 12.16 / H 4.65, C 69.62, N 11.76 |
| 5 | yellow crystals | 78 | (4-methylphenyl)-O-(CH2)3-phenyl | H | 212.5–213 (dec) (E/DMF) | 363(M⁺), 272, 268, 245, 176, 150, 121, 91, 65 | 3110, 3050, 2925, 2780, 2190, 1690, 1585, 1555, 1500, 1490, 1350, 1260, 1245, 1205, 1170, 1110, 820, 720, 535 | 1.50–2.37(2H, m), 2.37–2.91(2H, m), 4.01(2H, t, J=6Hz), 7.05(2H, d, J=8.5Hz), 7.22(5H, s), 7.54(2H, d, J=8.5Hz), 7.76(1H, s) | $C_{20}H_{17}N_3O_2S$ (363.441) | H 4.71, C 66.10, N 11.56 / H 4.85, C 66.05, N 11.53 |
| 6 | orange-yellow needles | 69 | (4-methylphenyl)-O-(4-chlorophenyl) | H | 225–226.5 (dec) (E/DMF) | 355(M⁺), 262, 260, 149 | 3160, 3075, 2945, 2770, 2200, 1720, 1590, 1580, 1500, 1480, 1355, 1290, 1245, 1205, 1190, 1170, 1090, 1010, 830, 545, 490 | 6.40–8.00(1H, br), 7.13(4H, dd, J=8.5Hz, 9Hz), 7.49(2H, d, J=9Hz), 7.67(2H, d, J=8.5Hz), 7.84(1H, s) | $C_{17}H_{10}ClN_3O_2S$ (355.805) | H 2.83, C 57.39, N 11.81 / H 3.13, C 57.44, N 11.54 |

TABLE 1-continued

| Ex No. | Descrip-tion | Yield (%) | R | R' | mp(°C.) (recryst solv*3) | EI-MS(m/z) | IR(KBr, cm⁻¹) | ¹H-NMR(DMSO-d6, δ: ppm) | Molecular formula (Molecular weight) | EA(%) Calcd./Found |
|---|---|---|---|---|---|---|---|---|---|---|
| 7 | orange crystals | 76 | 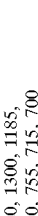 | H | 204.5–205.5 (dec) (E/DMF) | 337(M⁺), 242, 200, 197, 165 | 3125, 3040, 2930, 2750, 2200, 1730, 1700, 1615, 1600, 1580, 1545, 1490, 1470, 1405, 1355, 1320, 1300, 1185, 1080, 755, 715, 700 | 4.30–5.40(1H, br), 7.21(2H, d, J=9Hz), 7.40(5H, s), 7.50(2H, d, J=9Hz), 7.71(1H, s) | $C_{17}H_{11}N_3OS_2$ (337.427) | H 3.29, C 60.51, N 12.45 / H 3.57, C 60.27, N 12.38 |
| 8 | yellow crystals | 91 |  | H | 271–272 (E/DMF) | 349(M⁺), 254 | 3050, 2960, 2800, 2200, 1700, 1580, 1357, 1296, 1211, 1177, 754, 550 | 3.93(1H, br), 7.20–7.84(10H, m), 7.87(1H, s) | $C_{19}H_{12}FN_3OS$ (349.388) | H 3.46, C 65.32, N 12.03 / H 3.73, C 65.53, N 11.78 |
| 9 | orange-yellow plates | 62 | 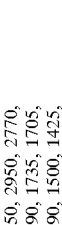 | H | 196–197.5 (E) | 349(M⁺), 254, 121, 149, 134, 221, 105, 79 | 3050, 2950, 2770, 2190, 1735, 1705, 1590, 1500, 1425, 1350, 1290, 1250, 1235, 1195, 1165, 1110, 830, 725 | 2.09, 2.27(each 3H, s), 6.30–8.50(1H, br), 6.85(1H, s), 6.99 (1H, d, J=7Hz, 2H, d, J=8.5Hz), 7.24(1H, d, J=7Hz 3-H), 7.62(1H, d, J=8.5Hz), 7.82(1H, s) | $C_{19}H_{13}N_3O_2S$ (349.414) | H 4.33, C 65.31, N 12.03 / H 4.50, C 64.91, N 11.66 |
| 10 | pale yellow crystals | 78 | 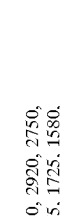 | H | 193–194 (dec) (I/DMF) | 349(M⁺), 150, 105, 79 | 3050, 2920, 2750, 2175, 1725, 1580, 1505, 1495, 1345, 1305, 1290, 1255, 1020, 535 | 3.08(2H, t, J=7Hz), 4.30(2H, t, J=7Hz), 6.30–8.30(1H, br), 7.12(2H, d, J=8Hz), 7 335H, s), 7.60(2H, d, J=8Hz), 7.82(1H, s) | $C_{19}H_{15}N_3O_2S$ (349.414) | H 4.33, C 65.31, N 12.03 / H 4.45, C 65.27, N 11.93 |

TABLE 2

| Ex. No. | Description | Yield (%) | R | R' | mp(°C.) (recryst solv*3) | EI-MS(m/z) | IR(KBr, cm⁻¹) | ¹H-NMR(DMSO-d6, δppm) | Molecular formula (Molecular weight) | EA(%) Calcd./Found |
|---|---|---|---|---|---|---|---|---|---|---|
| 11 | pale yellow crystals | 66 | 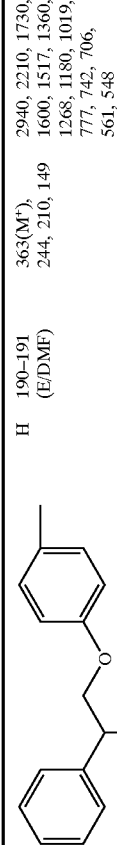 | H | 190–191 (E/DMF) | 363(M⁺), 244, 210, 149 | 2940, 2210, 1730, 1600, 1517, 1360, 1268, 1180, 1019, 777, 742, 706, 561, 548 | 1.34(3H, d, J=6.6Hz), 3.00–3.50(1H, m), 4.17(2H, d, J=6.6Hz), 5.10(1H, br), 7.09(2H, d, J=9Hz), 7.31(5H, s), 7.58(2H, d, J=9Hz), 7.80 (1H, s) | C₂₀H₁₇N₃O₂S (363.441) | H 4.71, C 66.10, N 11.56 / H 4.76, C 65.76, N 11.57 |
| 12 | pale yellow crystals | 80 |  | H | 172–173 (dec) (E/DMF) | 349(M⁺), 150, 105 | 3050, 3020, 2930, 2775, 2220, 1720, 1620, 1600, 1490, 1350, 1290, 1220, 1060, 1030, 990, 780, 750, 730, 700, 525 | 3.05(2H, t, J=7Hz), 4.24(2H, t, J=7Hz), 6.85–7.60(9H, m), 7.82(1H, s) | C₁₉H₁₅N₃O₂S (349.414) | H 4.33, C 65.31, N 12.03 / H 4.53, C 65.64, N 11.96 |
| 13 | yellow brown crystals | 60 | 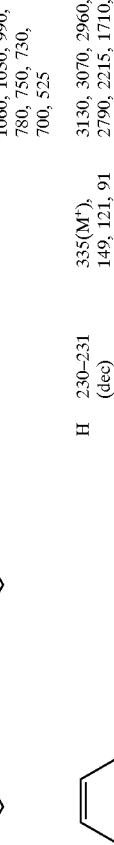 | H | 230–231 (dec) (E/DMF) | 335(M⁺), 149, 121, 91 | 3130, 3070, 2960, 2790, 2215, 1710, 1600, 1590, 1510, 1365, 1260, 1240, 1210, 1180, 985, 840, 765, 730, 595, 510 | 3.80–4.90(1H, br), 5.19(2H, s), 7.18(2H, d, J=9Hz), 7.42(5H, s), 7.60(2H, d, J=9Hz), 7.81(1H, s) | C₁₈H₁₃N₃O₂S (335.387) | H 3.90, C 64.46, N 12.53 / H 4.20, C 64.52, N 12.20 |
| 14 | yellow needles | 56 |  | H | 265(dec) (DMF) | 379(M⁺), 286, 284 | 3050, 2930, 2750, 2195, 1715, 1595, 1495, 1445, 1415, 1350, 1330, 1290, 1260, 1240, 1165, 1060, 1035, 800, 720, 560, 540 | 7.33(1H, dd, J=9Hz, 2.5Hz), 7.46–7.83(6H, m), 8.03(2H, d, J=8Hz) | C₁₉H₁₀ClN₃O₂S (379.827) | H 2.65, C 60.09, N 11.06 / H 3.06, C 60.51, N 10.91 |
| 15 | yellow crystals | quart. | 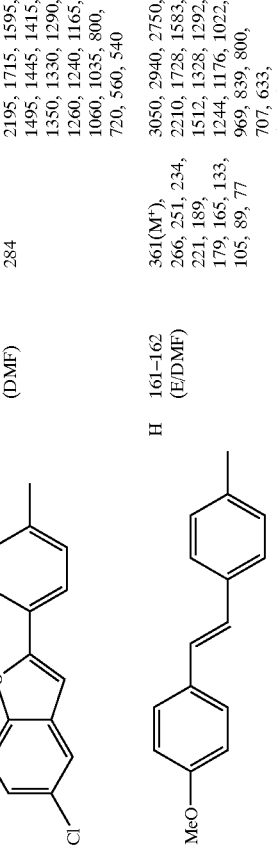 | H | 161–162 (E/DMF) | 361(M⁺), 266, 251, 234, 221, 189, 179, 165, 133, 105, 89, 77 | 3050, 2940, 2750, 2210, 1728, 1583, 1512, 1328, 1292, 1244, 1176, 1022, 969, 839, 800, 707, 633, 560, 542 | 3.81(3H, s), 6.87–7.90(11H, m)*4 | C₂₀H₁₅N₃O₂S·½H₂O (370.433) | H 4.35, C 64.85, N 11.34 / H 4.23, C 64.87, N 11.29 |
| 16 | Light-brown crystals | 93 |  | H | 202.5–203.5 (E/DMF) | 321(M⁺), 226, 197, 165 | 3025, 2920, 2750, 2200, 1733, 1630, 1600, 1485, 1340, 1286, 1260, 1220, 754, 720, 525 | 5.18(1H, br), 7.00–7.68(9H, m), 7.86(1H, s) | C₁₇H₁₁N₃O₂S (321.36) | H 3.45, C 63.54, N 13.08 / H 3.72, C 63.61, N 12.80 |

TABLE 2-continued

| Ex. No. | Description | Yield (%) | R | R' | mp(° C.) (recryst solv*3) | EI-MS(m/z) | IR(KBr, cm⁻¹) | ¹H-NMR(DMSO-d6, δppm) | Molecular formula (Molecular weight) | EA(%) Calcd./Found |
|---|---|---|---|---|---|---|---|---|---|---|
| 17 | yellow crystals | 95 | benzo[1,3]dioxol-5-ylmethoxy-phenyl | H | 217–218 (dec) (E/DMF) | 379(M⁺), 245, 150, 135, 105, 77 | 3050, 2950, 2775, 2200, 1700, 1585, 1510, 1445, 1355, 1300, 1255, 1215, 1175, 1040, 1020, 985, 930, 830, 810, 730, 550 | 3.60–4.70(1H, br), 5.05(2H, s), 5.95(2H, s), 6.80–7.05(3H, m), 7.13(2H, d, J=9Hz), 7.58 (2H, d, J=9Hz), 7.68(1H, s) | C₁₉H₁₃N₃O₄S (379.396) | H 3.45, C 60.15, N 11.08 / H 3.74, C 59.82, N 10.96 |
| 18 | light-orange crystals | 84 | 4-(4-methylbenzyloxy)phenyl | H | 248.5–249.5 (dec) (E/DMF) | 349(M⁺), 150, 105 | 3030, 2930, 2770, 2225, 2200, 1715, 1600, 1590, 1505, 1355, 1290, 1260, 1240, 1190, 1170, 990, 835, 800, 725, 555, 540, 480 | 2.31(3H, s), 4.60–6.20(1H, br), 5.13(2H, s), 7.00–7.47(6H, m), 7.60(2H, d, J=9Hz), 7.80(1H, s) | C₁₉H₁₅N₃O₂S (349.414) | H 4.33, C 65.31, N 12.03 / H 4.52, C 65.40, N 11.78 |
| 19 | orange crystals | 54 | 4-(4-chlorobenzyloxy)phenyl | H | 220–221 (dec) (E/DMF) | 369(M⁺), 149, 127, 125, 105 | 3050, 2930, 2780, 2225, 1720, 1620, 1610, 1595, 1510, 1360, 1290, 1260, 1245, 1200, 1175, 1000, 850, 840, 820, 720, 540, 510 | 3.90–5.00(1H, br), 5.20(2H, s), 7.19(2H, d, J=9Hz), 7.48(4H, s), 7.63(2H, d, J=9Hz), 7.82(1H, s) | C₁₈H₁₂ClN₃O₂S (369.832) | H 3.27, C 58.46, N 11.36 / H 3.52, C 58.65, N 11.09 |
| 20 | red crystals | 89 | 2-methoxy-4-methyl-styrylphenyl | H | 250.5(dec) (E/DMF) | 361(M⁺), 262, 234, 223, 206 | 3030, 2950, 2203, 1744, 1593, 1516, 1360, 1330, 1279, 1161, 1043, 970, 839, 763, 698, 637, 604, 555, 520 | 3.92(3H, s), 4.22(1H, br), 7.09–7.99(10H, m), 7.85(1H, s) | C₂₀H₁₅N₃O₂S (361.425) | H 4.18, C 66.47, N 11.63 / H 4.35, C 66.71, N 11.35 |

TABLE 3

| Ex. No. | Description | Yield (%) | R | R' | mp(°C.) (recryst solv*3) | EI-MS(m/z) | IR(KBr, cm⁻¹) | ¹H-NMR(DMSO-d6, δ ppm) | Molecular formula (Molecular weight) | EA(%) Calcd./Found |
|---|---|---|---|---|---|---|---|---|---|---|
| 21 | yellow crystals | 52 | 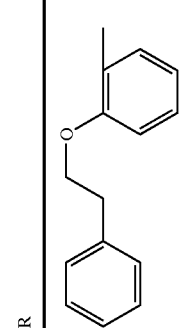 | H | 204–205.5 (dec) (E/DMF) | 349(M⁺), 178, 149, 105, 77 | 3010, 2910, 2760, 2200, 1725, 1620, 1610, 1590, 1480, 1445,1345, 1290, 1280, 1230, 1180, 1150, 750, 720, 690, 520 | 3.05(2H, t, J=6.5Hz), 4.25(2H, t, J=6.5Hz), 6.85–7.60(9H, m), 8.01(1H, s) | C₁₉H₁₅N₃O₂S (349.414) | H 4.33, C 65.31, N 12.03 / H 4.48, C 65.34, N 12.09 |
| 22 | pale yellow crystals | 84 | 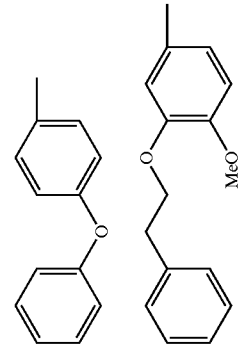 | H | 218–219 (dec) (E/DMF) | 321(M⁺), 226, 197, 149, 121, 77 | 3500–2700, 2200, 1730, 1580, 1505, 1490, 1360, 1295, 1260, 1200, 1170, 745, 530, 480 | 4.00–4.80(1H, br), 7.00–7.53(7H, m), 7.66(2H, d, J=9Hz), 7.84(1H, s) | C₁₇H₁₁N₃O₂S (321.36) | H 3.45, C 63.53, N 13.08 / H 3.79, C 63.69, N 12.93 |
| 23 | orange-yellow crystals | 84 | 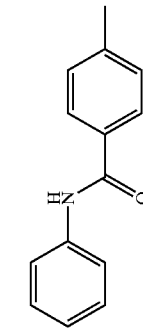 | H | 195–195.5 (E/DMF) | 379(M⁺), 274, 180, 105, 79 | 3050, 2950, 2790, 2195, 1720, 1700, 1590, 1580, 1510, 1435, 1340, 1270, 1250, 1220, 1170, 1145, 1020, 720, 545, 485 | 3.06(2H, t, J=7Hz), 4.22(3H, s), 3.83(3H, s), 6.95–7.50(8H, m), 7.77(1H, s) | C₂₀H₁₇N₃O₃S (379.44) | H 4.52, C 63.31, N 11.07 / H 4.73, C 63.64, N 11.00 |
| 24 | pale yellow crystals | 59 | 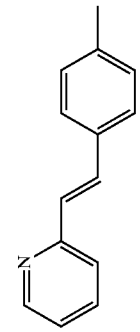 | H | 275(dec) (E/DMF) | 348(M⁺), 256, 161, 133, 91 | 3050, 2950, 2770, 2190, 1735, 1650, 1595, 1530, 1500, 1440, 1345, 1320, 1295, 1240, 1180, 770, 720, 690, 585, 565, 540 | 4.15–5.40(2H, br), 6.95–7.62(3H, m), 7.62–8.30(7H, m) | C₁₈H₁₂N₄O₂S (348.386) | H 3.47, C 62.06, N 16.08 / H 3.71, C 62.11, N 15.92 |
| 25 | yellow crystals | 79 | 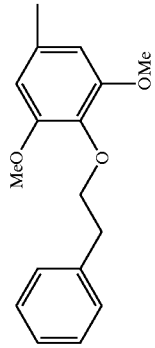 | H | 295–296 (dec) (DMF) | 331[(M − 1)⁺], 236, 204, 158, 113, 79, 51 | 3050, 2925, 2900–2300, 2175, 1730, 1640, 1610, 1510, 1470, 1425, 1320, 1300, 1270, 1250, 1210, 1175, 980, 820, 600, 545 | 7.30–8.90(m) | C₁₈H₁₂N₄OS · ⅓H₂O (338.392) | H 3.77, C 63.89, N 16.56 / H 4.03, C 63.70, N 16.32 |
| 26 | yellow crystals | 65 | (MeO, OMe structure) | H | 194–195 (E) | 409(M⁺), 305, 210, 105, 79 | 3050, 3025, 2940, 2830, 2760, 2195, 1730, 1700, 1600, 1500, 1450, 1420, 1320, 1240, 1185, 1155, 1130, 990, 730, 700, 560, 545, 530 | 2.97(2H, t, J=7Hz), 3.81(6H, s), 4.18(2H, t,J=7Hz), 6.90(2H, s), 7.10–7.40(5H, m), 7.80(1H, s) | C₂₁H₁₉N₃O₄S (409.466) | H 4.68, C 61.60, N 10.26 / H 4.75, C 61.64, N 10.19 |

TABLE 3-continued

| Ex. No. | Description | Yield (%) | R | R' | mp(° C.) (recryst solv*3) | EI-MS(m/z) | IR(KBr, cm⁻¹) | ¹H-NMR(DMSO-d6, δ ppm) | Molecular formula (Molecular weight) | EA(%) Calcd./Found |
|---|---|---|---|---|---|---|---|---|---|---|
| 27 | orange plates | 79 | (4-methylphenyl-N(CH₃)-C(O)-phenyl) | H | 202.5–203.5 (dec) (E) | 362(M⁺), 105, 77 | 3050, 2935, 2755, 2195, 1730, 1600, 1515, 1350, 1300, 1290(sh), 1245, 1180, 1105, 720 | 3.42(3H, s), 5.50–6.40(1H, br), 7.28(1H, s), 7.30(2H, d, J=8Hz), 7.54(2H, d, J=8Hz), 7.78(1H, s) | C₁₉H₁₄N₄O₂S · ½C₂H₅OH (385.448) | H 4.45, C 62.32, N 14.54 / H 4.56, C 62.19, N 14.16 |
| 28 | light brown crystals | 95 | (2-fluoro-4-bromobenzyloxy-4-methylphenyl) | H | 270–271 (E/DMF) | 433[(M + 2)⁺], 431(M⁺), 189, 187, 149, 107 | 3060, 2940, 2800, 2230, 1720, 1635, 1618, 1600, 1520, 1361, 1298, 1273, 1255, 1180, 1002, 897, 852, 840, 540 | 3.62(1H, br), 5.22(2H, s), 7.23(2H, d, J=9Hz), 7.42–7.78(5H, m), 7.83 (1H, s) | C₁₈H₁₁BrFN₃O₂S (432.273) | H 2.56, C 50.01, N 9.72 / H 2.87, C 50.22, N 9.68 |
| 29 | orange crystals | 65 | (3-(4-methylbenzylidene)-2-oxoindoline) | H | >300 (E/DMF) | 372(M⁺), 277 | 3320, 3050, 2940, 2750, 2190, 1720, 1690, 1640, 1590, 1465, 1380, 1345, 1330, 1290, 1245, 1190, 1100, 795, 760, 725, 600, 525 | | C₂₀H₁₂N₄O₂S · ½C₃H₇NO (408.956) | H 3.82, C 63.15, N 15.41 / H 4.12, C 62.96, N 15.40 |
| 30 | pale yellow crystals | 68 | (2-(4-methylbenzylidene)-indan-1-one) | H | >300 (DMF) | 371(M⁺), 276, 247, 213, 139, 114, 89 | 3050, 2930, 2770, 2190, 1730, 1690, 1610, 1590, 1505, 1415, 1345, 1325, 1290, 1265, 1240, 1195, 1180, 1090, 735, 720, 600, 540 | | C₂₁H₁₃N₃O₂S (371.42) | H 3.53, C 67.91, N 11.31 / H 3.88, C 68.11, N 11.12 |

TABLE 4

| Ex. No. | Description | Yield (%) | R | R' | mp(°C.) (recryst solv*3) | EI-MS(m/z) | IR(KBr, cm⁻¹) | ¹H-NMR(DMSO-d6, δ:ppm) | Molecular formula (Molecular weight) | EA(%) Calcd./Found |
|---|---|---|---|---|---|---|---|---|---|---|
| 31 | yellow crystals | 79 | (benzothiazole-styryl-p-tolyl) | H | >300 (DMF) | 388(M⁺), 294, 292, 260, 249, 236, 163, 149, 77 | 3050, 3020, 2950, 2750, 2190, 1725, 1595, 1510, 1415, 1350, 1320, 1290, 1240, 1190, 1175, 760, 720, 565, 550 | 7.40–8.50(m) | $C_{20}H_{12}N_4OS_2 \cdot$ ⅓$C_3H_7NO$ (412.84) | H 3.50, C 61.10, N 14.70 / H 3.71, C 61.02, N 14.57 |
| 32 | pale yellow crystals | 70 | (C₂H₅-CH(OPh)-p-tolyl) | H | 144–145.5 (EA/H) | 363(M⁺), 244, 210, 149 | 2960, 2930, 2200, 1730, 1598, 1507, 1357, 1259, 1177, 1000, 978, 829, 705, 523 | 0.90(3H, t, J=7.2Hz), 1.61–2.10(2H, m), 4.40(1H, br), 5.35(1H, t, J=6.2Hz), 7.05(2H, d, J=8.4Hz), 7.33(5H, s), 7.50(2H, d, J=8.4Hz), 8.73(1H, s) | $C_{20}H_{17}N_3O_2S$ (363.441) | H 4.71, C 66.10, N 11.56 / H 4.89, C 66.00, N 11.38 |
| 33 | yellow crystals | 94 | (p-tolyl-O-phenyl) | H | 238.5–240 (E/DMF) | 335(M⁺), 250, 240, 173, 147 | 3040, 2945, 2770, 2205, 1730, 1603, 1498, 1358, 1338, 1300, 1250, 1180, 810, 753, 514 | 5.19(2H, s), 5.53(1H, br), 6.94–7.53(5H, m), 7.63(4H, s), 7.86(1H, s) | $C_{18}H_{13}N_3O_2S$ (335.387) | H 3.91, C 64.46, N 12.53 / H 4.07, C 64.44, N 12.17 |
| 34 | yellow crystals | 93 | (biphenyl-p-tolyl) | H | 253.5–255 (E/DMF) | 305(M⁺), 210 | 3045, 2950, 2750, 2200, 1737, 1595, 1490, 1339, 1179, 770, 640, 560, 547 | 4.32(1H, br), 7.33–7.95(9H, m), 7.91(1H, s) | $C_{17}H_{11}N_3OS$ (305.361) | H 3.63, C 66.87, N 13.76 / H 3.96, C 66.93, N 13.70 |
| 35 | orange crystals | 82 | (isopropyl-phenyl-styryl-p-tolyl) | H | 240(dec) (E/A) | 373(M⁺), 358, 278, 263, 230, 202, 129,91, 68 | 3020, 2955, 2760, 2200, 1730, 1585, 1510, 1340, 1295, 1245, 1190, 1170, 830, 555 | 1.20(6H, d, J=7Hz), 2.92(1H, septet), 3.60–4.50(1H, br), 7.15–7.90(11H, m) | $C_{22}H_{19}N_3OS$ (373.48) | H 5.13, C, 70.75, N 11.25 / H 5.29, C 70.81, N 11.21 |
| 36 | pale yellow crystals | 85 | (p-tolyl-O-CH₂-CH=CH-phenyl) | H | 219.5–220.5 (dec) (E/DMF) | 361(M⁺), 150, 117, 91 | 3100, 3050, 2950, 2780, 2195, 1710, 1590, 1580, 1560, 1510, 1360, 1250, 1205, 1175, 1000, 970, 835, 730, 550 | 3.50–5.00(1H, br), 4.83(2H, d, J=5 Hz), 6.45–6.80(2H, m), 7.18(2H, d, J=9Hz), 6.90–7.80(5H, m), 7.63 (2H, d, J=9Hz, 2,6-H), 7.82(1H, s) | $C_{20}H_{15}N_3O_2S$ (361.425) | H 4.19, C 66.50, N 11.63 / H 4.40, C 66.46, N 11.41 |

TABLE 4-continued

| Ex. No. | Description | Yield (%) | R | R' | mp(° C.) (recryst solv*3) | EI-MS(m/z) | IR(KBr, cm⁻¹) | ¹H-NMR(DMSO-d6, δ:ppm) | Molecular formula (Molecular weight) | EA(%) Calcd./Found |
|---|---|---|---|---|---|---|---|---|---|---|
| 37 | yellow crystals | 37 | (structure: bis-phenethyloxy benzene) | H | 161.5–162.5 (E) | 469(M⁺), 364, 267, 105, 77 | 3050, 3005, 2930, 2750, 2190, 1720, 1590, 1500, 1460, 1345, 1300, 1270, 1250, 1210, 1165, 1135, 1010, 745, 715, 690 | 3.04(4H, t, J=6.5Hz), 4.00–4.45(4H,m), 6.90–7.60(13H, m), 7.78(1H, s) | $C_{27}H_{23}N_3O_3S$ (469.565) | H 4.94, C 69.06, N 8.95 / H 5.09, C 69.02, N 8.64 |
| 38 | orange-yellow crystals | 73 | (structure: HO-methylphenyl-O-phenethyl) | H | 189.5–190.5 (dec) (M) | 365(M⁺), 166, 105, 79 | 3050, 2930, 2770, 2200, 1720(sh), 1710, 1595, 1505, 1455, 1360, 1280, 1250, 1210, 1170, 1135, 1010, 720, 700, 510 | 3.09(2H, t, J=7Hz), 4.27(2H, t, J=7Hz), 6.90–7.55 (8H, m), 7.71(1H, s) | $C_{19}H_{15}N_3O_3S$ (365.413) | H 4.14, C 62.45, N 11.50 / H 4.30, C 62.16, N 11.13 |
| 39 | orange-yellow crystals | 57 | (structure: benzamide-tolyl) | H | 297(dec) (E/DMF) | 348(M⁺), 197, 148, 105 | 3060, 2950, 2930, 2770, 2195, 1720, 1705, 1655, 1590, 1510, 1485, 1415, 1350, 1320, 1295, 1240, 1185, 710, 630, 610, 535 | 7.40–8.20(m) | $C_{18}H_{12}N_4O_2S$ (348.386) | H 3.47, C 62.06, N 16.08 / H 3.74, C 62.12, N 15.86 |
| 40 | orange crystals | 55 | (structure: fluorenylidene-methylphenyl) | H | 257–259 (dec) (E/DMF) | 405(M⁺), 310, 253, 165 | 3050, 2950, 2760, 2200, 1715, 1595, 1445, 1350, 1290, 1240, 1190, 1170, 775, 730, 610, 540 | 3.50–4.35(1H, br), 6.95–8.15(14H, m) | $C_{25}H_{15}N_3OS \cdot C_2H_5OH$ (451.55) | H 4.69, C 71.82, N 9.31 / H 4.80, C 72.12, N 9.18 |
| 41 | yellow crystals | 80 | (structure: tolyl-O-ethyl-O-phenyl) | H | 225–226.5 (dec) (E/DMF) | 365(M⁺), 270, 245, 176, 150, 121, 93, 77 | 3120, 3060, 2945, 2780, 2190, 1710, 1600, 1505, 1485, 1450, 1360, 1260, 1250, 1230, 1200, 1170, 1065, 955, 830, 760, 725, 540 | 4.37(4H, br), 6.80–7.47 (7H, m), 7.47–7.75(3H, m)*⁴ | $C_{19}H_{15}N_3O_3S$ (365.413) | H 4.14, C 62.45, N 11.50 / H 4.32, C 62.39, N 11.44 |

TABLE 5

| Ex. No. | Description | Yield (%) | R | R' | mp(°C.) (recryst solv*³) | EI-MS(m/z) | IR(KBr, cm⁻¹) | ¹H-NMR(DMSO-d6, δ: ppm) | Molecular formula (Molecular weight) | EA(%) Calcd./Found |
|---|---|---|---|---|---|---|---|---|---|---|
| 42 | orange crystals | 76 | 3-methyl-4-methoxystyryl (structure) | H | 273–275 (dec) (E/DMF) | 361(M⁺), 189, 177, 165, 147 | 3045, 2975, 2210, 1710, 1600, 1512, 1365, 1282, 1252, 1219, 1199, 1036, 970, 823, 730, 540 | 3.93(3H, s), 5.25(1H, br), 7.11–7.92(10H, m), 7.93(1H, s) | $C_{20}H_{15}N_3O_2S$ (361.425) | H 4.18, C 66.47, N 11.63 / H 4.44, C 66.43, N 11.27 |
| 43 | yellow crystals | 76 | (structure) | H | 206–207 (dec) (E) | 365(M⁺), 166, 105, 79 | 3050, 2940, 2760, 2195, 1705, 1570, 1510, 1350, 1300, 1285, 1220, 1190, 1125, 720, 695 | 3.10(2H, t, J=7Hz), 4.27 (2H, t, J=7Hz), 6.90–7.60(8H, m), 7.79(1H, s) | $C_{19}H_{15}N_3O_3S$ (365.413) | H 4.14, C 62.45, N 11.50 / H 4.28, C 62.26, N 11.33 |
| 44 | brown crystals | 49 | (structure with H₅C₂) | H | 198–200 (E/DMF) | 359(M⁺), 344, 330, 283, 264, 249, 216, 188, 147, 129, 116, 114, 91 | 3050, 2955, 2760, 2200, 1733, 1597, 1350, 1297, 1223, 1190, 700 | 1.01(3H, t, J=7Hz), 2.52(2H, m), 4.19(1H, br), 6.54(1H, s), 6.92–7.69(9H, m), 7.73(1H, s) | $C_{21}H_{17}N_3OS$ (359.453) | H 4.77, C 70.17, N 11.69 / H 4.96, C 70.15, N 11.52 |
| 45 | yellow crystals | 85 | (biphenyl structure) | H | 242–243 (E/DMF) | 305(M⁺), 304, 210, 165 | 3130, 3060, 2980, 2200, 1703, 1604, 1594, 1353, 1240, 760, 720, 700, 542 | 5.43(1H, br), 7.38–7.93(9H, m), 7.96(1H, s) | $C_{17}H_{11}N_3OS$ (305.361) | H 3.63, C 66.87, N 13.76 / H 3.99, C 66.96, N 13.49 |
| 46 | reddish brown crystals | 55 | (structure with MeO) | H | 183.5–185 (E/DMF) | 379(M⁺), 289, 273, 244, 178, 147, 91 | 3080, 2955, 2205, 1735, 1597, 1502, 1363, 1274, 1205, 1140, 1110, 1037, 742, 560, 493 | 3.87(3H, s), 4.56(2H, s), 4.62(2H, s), 7.04–7.71(8H, m), 7.80(1H, s) | $C_{20}H_{17}N_3O_3S$ (379.44) | H 4.52, C 63.31, N 11.07 / H 4.64, C 63.20, N 10.79 |

TABLE 5-continued

| Ex. No. | Description | Yield (%) | R | R' | mp(° C.) (recryst solv*3) | EI-MS(m/z) | IR(KBr, cm−1) | 1H-NMR(DMSO-d6, δ: ppm) | Molecular formula (Molecular weight) | EA(%) Calcd./Found |
|---|---|---|---|---|---|---|---|---|---|---|
| 47 | yellow crystals | 62 | (1,2-diphenylvinyl-p-tolyl) | H | 238–239 (E/DMF) | 407(M+), 312, 235, 203 | 3050, 2200, 1736, 1600, 1500, 1343, 1330, 1297, 1188, 772, 707, 640, 616, 550 | 4.55(1H, br), 6.89–7.60 (15H, m), 7.77(1H, s) | $C_{25}H_{17}N_3OS$ (407.497) | H 4.20, C 73.69, N 10.31 / H 4.47, C 73.83, N 10.00 |
| 48 | pale yellow crystals | 71 | (phthalimidoethoxy-p-tolyl) | H | 235–236 (dec) (E/DMF) | 418(M+), 174, 130, 78 | 3050, 2950, 2760, 2195, 1770, 1710, 1590, 1510, 1390, 130, 1250, 1170, 1120, 720 | 3.90–4.50(4H, m), 7.04(2H, d, J=8.5Hz), 7.53(2H, d, J=8.5Hz), 7.60(1H, s), 7.88(4H, s)*4 | $C_{21}H_{14}N_2O_4S$ (418.4330) | H 3.37, C 60.28, N 13.39 / H 3.62, C 60.27, N 13.10 |
| 49 | pale yellow crystals | 70 | (benzothiazolylthiomethyl-p-tolyl) | H | 200–201.5 (E/DMF) | 408(M+), 375, 280, 242, 147, 91 | 3060, 2930, 2750, 2190, 1730, 1640, 1455, 1430, 1350, 1295, 1245, 1195, 1180, 1000, 760, 715, 545 | 4.71(2H, s), 7.18–7.80(8H, m), 7.80– 8.10(2H, m)*4 | $C_{19}H_{12}N_4OS_3 \cdot ⅔C_3H_7NO$ (457.26) | H 3.67, C 55.16, N 14.30 / H 3.75, C 55.46, N 14.00 |
| 50 | yellow crystals | 79 | (4-chlorostyryl-p-tolyl) | H | >300 (DMF) | 365(M+), 272, 270, 234, 202, 178 | 3040, 2930, 2760, 2220, 1736, 1617, 1590, 1357, 1298, 1181, 1094, 838, 734, 538 | 3.92(1H, br), 7.20–7.87(10H, m), 7.83(1H, s) | $C_{19}H_{12}ClN_3OS$ (365.844) | H 3.31, C 62.38, N 11.49 / H 3.53, C 62.48, N 11.46 |
| 51 | yellow amorphous | 18*1 | (phenethoxy-p-tolyl) | Me | 69–71 | 363(M+), 164 | 3070, 2950, 2200, 1722, 1600, 1515, 1342, 1250, 1178, 1020, 836, 754, 700, 540 | 2.67(3H, s), 3.06(2H, t, J=6Hz), 3.86(1H, br), 4.28(2H, t, J=6Hz), 7.06(2H, d, J=9Hz), 7.30(5H, s), 7.46(2H, d,J=9Hz) | $C_{20}H_{17}N_3O_2S \cdot ¼H_2O$ (367.945) | H 4.79, C 65.29, N 11.42 / H 4.86, C 65.47, N 11.02 |
| 52 | yellow crystals | 91 | (4-trifluoromethylstyryl-p-tolyl) | H | 275–280 (dec) (E/DMF) | 399(M+), 304, 259, 227 | 3050, 2940, 2770, 2220, 1740, 1620, 1600, 1323, 1300, 1180, 1121, 1070, 838, 727, 526 | 4.40(1H, br), 7.45(2H, s), 7.50– 7.90(8H, m), 7.83(1H, s) | $C_{20}H_{12}F_3N_3OS$ (399.393) | H 3.03, C 60.15, N 10.52 / H 3.25, C 60.28, N 10.63 |

TABLE 6

| Ex. No. | De-scription | Yield (%) | R | R' | mp(°C.) (recryst solv*³) | EI-MS(m/z) | IR(KBr, cm⁻¹) | ¹H-NMR(DMSO-d6, δ: ppm) | Molecular formula (Molecular weight) | EA(%) Calcd./Found |
|---|---|---|---|---|---|---|---|---|---|---|
| 53 | pale yellow crystals | 94 | 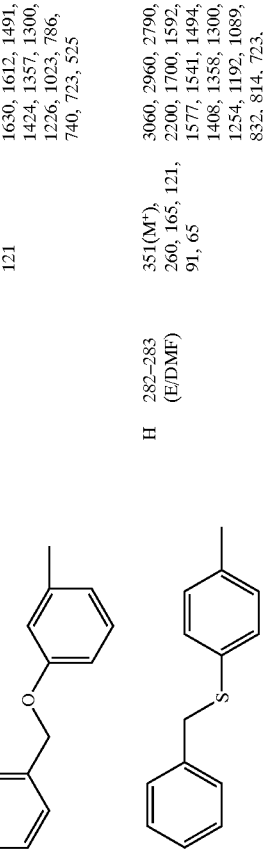 | H | 201–202.5 (E/DMF) | 335(M⁺), 245, 177, 149, 121 | 3030, 2920, 2770, 2210, 2200, 1720, 1630, 1612, 1491, 1424, 1357, 1300, 1226, 1023, 786, 740, 723, 525 | 5.18(2H, s), 5.70(1H, br), 7.02–7.65(9H, m), 7.80(1H, s) | $C_{18}H_{13}N_3O_2S$ (335.387) | H 3.91, C 64.46, N 12.53 / H 4.09, C 64.35, N 12.37 |
| 54 | yellow crystals | 73 | 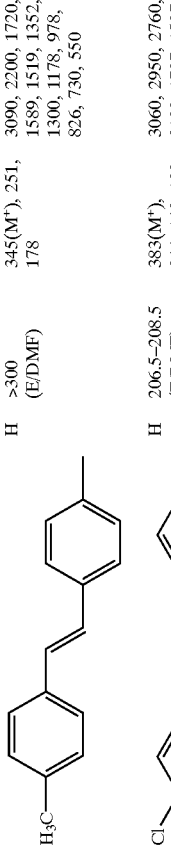 | H | 282–283 (E/DMF) | 351(M⁺), 260, 165, 121, 91, 65 | 3060, 2960, 2790, 2200, 1700, 1592, 1577, 1541, 1494, 1408, 1358, 1300, 1254, 1192, 1089, 832, 814, 723, 589, 570, 554, 525, 437 | 3.60(1H, br), 4.32(2H, s), 7.15–7.58(9H, m), 7.77(1H, s) | $C_{18}H_{13}N_3OS_2$ (351.454) | H 3.73, C 61.52, N 11.96 / H 3.97, C 61.53, N 12.04 |
| 55 | yellow crystals | 86 | 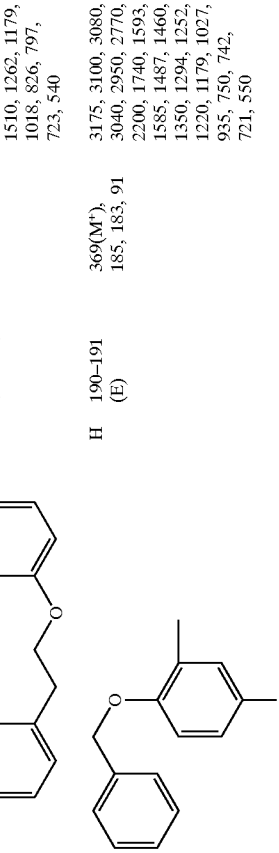 | H | >300 (E/DMF) | 345(M⁺), 251, 178 | 3090, 2200, 1720, 1589, 1519, 1352, 1300, 1178, 978, 826, 730, 550 | 2.32(3H, s), 5.13(1H, s), 7.10–7.73(11H, m)*⁴ | $C_{20}H_{15}N_3OS$ (345.426) | H 4.38, C 69.54, N 12.16 / H 4.66, C 70.12, N 11.48 |
| 56 | orange crystals | 69 | 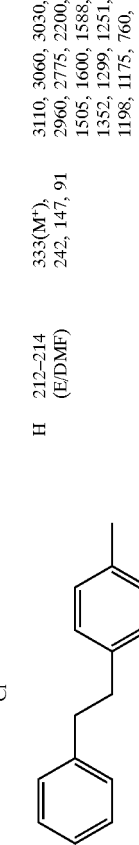 | H | 206.5–208.5 (E/DMF) | 383(M⁺), 244, 149, 139 | 3060, 2950, 2760, 2180, 1727, 1587, 1510, 1262, 1179, 1018, 826, 797, 723, 540 | 3.08(2H, t, J=6.8Hz), 4.30(2H, t, J=6.8Hz), 4.30(1H, br), 7.13(2H, d, J=9Hz), 7.38(4H, s), 7.62(2H, d, J=9Hz), 7.83(1H, s) | $C_9H_{14}ClN_3O_2S$ (383.859) | H 3.68, C 59.45, N 10.95 / H 3.87, C 59.67, N 10.65 |
| 57 | yellow crystals | 79 |  | H | 190–191 (E) | 369(M⁺), 185, 183, 91 | 3175, 3100, 3080, 3040, 2950, 2770, 2200, 1740, 1593, 1585, 1487, 1460, 1350, 1294, 1252, 1220, 1179, 1027, 935, 750, 742, 721, 550 | 3.80–5.80(1H, br), 5.26(2H, s), 7.10–7.70(8H, m), 7.91(1H, s) | $C_{18}H_{12}ClN_3O_2S$ (369.832) | H 3.27, C 58.46, N 11.36 / H 3.49, C 58.35, N 10.98 |
| 58 | pale yellow crystals | 64 |  | H | 212–214 (E/DMF) | 333(M⁺), 242, 147, 91 | 3110, 3060, 3030, 2960, 2775, 2200, 1505, 1600, 1588, 1505, 1352, 1299, 1251, 1198, 1175, 760, 728, 700 | 2.92(4H, s), 7.00–7.70(9H, m), 7.82(1H, s) | $C_{19}H_{15}N_3OS$ (333.415) | H 4.53, C 68.45, N 12.60 / H 4.72, C 68.70, N 12.37 |

TABLE 6-continued

| Ex. No. | Description | Yield (%) | R | R' | mp(° C.) (recryst solv*[3]) | EI-MS(m/z) | IR(KBr, cm$^{-1}$) | $^1$H-NMR(DMSO-d6, δ; ppm) | Molecular formula (Molecular weight) | EA(%) Calcd./Found |
|---|---|---|---|---|---|---|---|---|---|---|
| 59 | yellow crystals | 45 | (3-methylstyryl group) | H | 247–248 (E/DMF) | 331(M$^+$), 236, 203, 147, 103 | 3120, 3078, 3055, 3024, 2966, 2790, 2200, 1729, 1705, 1609, 1590, 1355, 1314, 1294, 1265, 1245, 1225, 1200, 1165, 960, 788, 755, 720, 689, 528 | 5.30–6.40(1H, br), 7.10–8.00(12H, m) | C$_{19}$H$_{13}$N$_3$OS (331.399) | H 3.95, C 68.86, N 12.68 / H 4.24, C 68.90, N 12.27 |
| 60 | orange-yellow crystals | 80 | (4-methyl-2-benzyloxy-5-methylphenyl group) | H | 227–228 (dec) (E/A) | 363(M$^+$), 177, 91 | 3060, 3040, 2950, 2775, 2195, 1730, 1685, 1590, 1505, 1310, 1270, 1230, 1095, 995, 730 | 2.22, 2.39(each 3H, s), 5.19(2H, s), 7.07(1H, s), 7.19(1H, s), 7.23–7.65(5H, m), 7.86(1H, s) | C$_{20}$H$_{17}$N$_3$O$_2$S (363.441) | H 4.71, C 66.10, N 11.56 / H 4.97, C 66.34, N 11.34 |
| 61 | yellow brown crystals | 83*[2] | (4-methoxy-4'-methylstilbene group) | Me | 203–204 (E/DMF) | 375(M$^+$), 280, 266, 250, 232, 221, 210, 166 | 3060, 3020, 2930, 2827, 2765, 2189, 1716, 1592, 1519, 1334, 1250, 1216, 1173, 1027, 968, 833, 563, 539 | 2.71(3H, s), 3.78(3H, s), 6.75–7.85(10H, m) | C$_{21}$H$_{17}$N$_3$O$_2$S · ⅓H$_2$O (381.457) | H 4.67, C 66.12, N 11.02 / H 4.92, C 66.22, N 10.80 |

EXAMPLE 2

2-(N-Cyanoimino)-5-[(E)-4-stylylbenzylidene]
thiazolidin-4-one Potassium Salt: Potassium Salt of
the Compound 1

The crude product (18.98 g) was recrystallized from 65% isopropanol to yield the title compound as yellow powder (10.87 g) (compound 62).

mp: >300° C. (60% Isopropanol)

IR (KBr, cm$^{-1}$): 3025, 2180, 1650, 1590, 1490, 1420, 1340, 1290, 1205, 1180, 960, 820, 745, 540

NMR (DMSO-d6, ppm): δ=7.25–7.55 (6H, m), 7.55–7.85 (6H, m)

EXAMPLE 3

2-(N-Cyanoimino)-5-[(E)-4-stylylbenzylidene]
thiazolidin-4-one Sodium Salt: Sodium Salt of the
Compound 1

100 g (0.3 mol) of compound 1 was dissolved in DMF. To a stirred solution of compound 1, 12.6 g (0.3 mol) of sodium hydroxide in 50 mL of water, and then activated charcoal was added. The activated charcoal was filtered off and the filtrate was concentrated under reduced pressure. The crude product was collected by filtration, washed with methanol and ether, and recrystallized from isopropanol/2-butanol/water to yield the title compound as yellow powder (69.9 g) (compound 63).

mp: >300° C. (Isopropanol/2-butanol/water)

IR (KBr, cm$^{-1}$): 3025, 2180, 1650, 1585, 1495, 1420, 1340, 1280, 1205, 1180, 960, 815, 745, 540

NMR (DMSO-d6, ppm): δ=7.25–7.52 (6H, m), 7.52–7.85 (6H, m)

EXAMPLE 4

Blood Sugar Lowering Actions in Genetically
Diabetic Mice

Genetically diabetic db/db mice (C57BL/ksJ Jcl-dbm db/db mice) older than 8 weeks were grouped depend on their blood sugar levels of the prior measurements in order to divide groups with almost equal mean value of the sugar level. The respective groups of db/db mice were designates as the following groups: the group given the compound of the present invention, the group of troglitazone, and the group given no administrating group. For the compounds of the present invention, two doses: 75 mg/kg and 150 mg/kg, and for troglitazone, a dose of 150 mg/kg were individually given to the mice as a forced oral administration once daily for 14 days successively. These agents were suspended in 3.0% Arabic gum solution for administration. To the control group, only the same volume of 3.0% Arabic gum solution was administered. On the next day of the final administration, each mouse was bred for sampling. The blood samples were subject to serum separation. The glucose level in the serum of each group was measured. Then, a reduction rate in a glucose level (%) compared to the control group was calculated with mean value of each group according to the equation below. As a result, it was demonstrated that the compounds of the present invention have the activity to reduce blood sugar levels more effectively than troglitazone (Table 7).

Equation: Reduction rate (%) =

$$\left(1 - \frac{\text{(mean measured level in each treated group)}}{\text{(mean measured level in control group)}}\right) \times 100$$

TABLE 7

Blood sugar lowering effects in genetically diabetic mice

| Compound No. | Dose | Reduction in Blood Glucose (%) |
|---|---|---|
| 1 | 75 mg/kg | 31 |
|  | 150 mg/kg | 37 |
| 3 | 75 mg/kg | 24 |
|  | 150 mg/kg | 49 |
| 22 | 75 mg/kg | 16 |
|  | 150 mg/kg | 34 |
| 63 | 75 mg/kg | 32 |
| troglitazone | 150 mg/kg | 18 |

EXAMPLE 5

Differentiation-Inducing Actions on Adipose Cells

The cloned cell line 3T3–L1 of the preadipocyte cells at the 9–20$^{th}$ generation were used. The cell suspension at a concentration of 2×10$^4$ cells/ml was added 500 μl/well in a 24 well microplate. Then, the microplates were cultured at 37° C. in the atmosphere of 5% CO$_2$ for 4 days with D-MEM containing 5% inactivated fetal calf serum (hereinafter abbreviated as "FCS D-MEM"). Next, the following procedures were conducted.

(1) To test compound of this invention, 500 μl/well of the following solutions was added to each well:

1) test compound-containing medium (T-MEM) in which the test compound in a stock solution (30 mM in DMSO) was diluted with FCS D-MEM containing 0.1 μM dexamethazone and 100 ng/ml insulin (hereinafter abbreviated as DEX-Ins-FCS D-MEM);

2) FCS-D-MEM; 3) DEX-Ins-FCS D-MEM; 4) 0.1% DMSO-containing DEX-Ins-FCS D-MEM for me control wells.

(2) After above additions were done, the culture plates were incubated at 37° C. in 5% CO$_2$ for 3 days. Then, the same operations as in the procedure (1) were repeated for exchange of the culture medium. The culture plates were incubated at 37° C. in 5% CO$_2$ for further 3 days.

(3) After incubation, the culture medium was removed from the culture plates. Then, the FCS D-MEM was added to the FCS D-MEM-wells, and next the medium prepared for containing 100 ng/ml of insulin with the FCS D-MEM (hereinafter abbreviated as "Ins-FCS D-MEM") was added at 500 μl/well to the T-MEM wells and DEX-Ins-FCS D-MEM wells. All culture plates were incubated for 4 days.

(4) After incubation, the culture medium was removed. For cell fixation, 500 μl/well of 10% formalin in neutral buffer was added, and left at the room temperature for approximately 20 minutes or longer. Then the formalin solution was removed, and 60% 2-propanol solution was added at 500 μl/well, then quickly removed, and the oil red-O staining solution was added at 250 μl/well. The culture plates were sealed with plate seals, and left at room temperature for 30 minutes or longer. After incubation, the staining solution was removed, and the 60% 2-propanol solution was added at 500 μl/well, and quickly removed. The cells were rinsed with water a few times, and then water drops were flipped away. A cell-lysis buffer was added at 500 μl/well, and the culture plates were sealed with plate seals, and left at 37° C. for 1 hour to extract the pigments. Next, 300 μl/well of the extract solution was transferred at a 96 well micro-plates, and then the absorbance of each extract was measured at wavelength of 490 nm.

The absorbance ratios of the respective test compounds-groups to the control group, the mean absorbance of which was designated as 1.0, are shown in Table 8. Based on the judgement that the absorbance higher than that of the control group indicates a greater differentiation-inducing activity of the test compound, the compounds of the present invention were determined to have the activity to induce differentiation of preadipocytes to adipocytes, resulting in elevating insulin sensitivity of organs. Thereby, this activity would confer the efficacy in the therapy of diabetes.

TABLE 8

Activities to induce differentiation of preadipocytes to adipocytes

| Compound No. | Absorbance Ratio | Compound No. | Absorbance Ratio |
| --- | --- | --- | --- |
| 1 | 1.46 | 16 | 1.18 |
| 2 | 1.57 | 19 | 1.51 |
| 3 | 1.48 | 21 | 2.02 |
| 4 | 2.62 | 22 | 1.73 |
| 5 | 1.87 | 26 | 1.09 |
| 7 | 1.93 | 34 | 1.40 |
| 8 | 1.95 | 42 | 2.01 |
| 10 | 2.12 | 44 | 1.83 |
| 12 | 1.74 | 45 | 1.14 |
| 13 | 2.51 | 47 | 1.24 |
| Control | 1.00 | | |

EXAMPLE 6

Antihyperlipidemic Activities in Genetically Diabetic Mice

In the same way as described in EXAMPLE 4, db/db mice were grouped in the manner by which the respective groups had almost equivalent mean blood sugar levels. The compounds 1, 3, 13, 21 and 22 of the present invention, suspended in 3.0% Arabic gum solution, were orally administrated, with a dose of 150 mg/kg, once daily for successive 14 days. The control group of mice were given the vehicle solution only. On the next day of the final administration, each mouse was bled for sampling. The blood was subjected for serum separation, and then subjected to measurements of β-lipoproteins, free fatty acids, and triglycerides. The reduction rate (%) of each measurement compared to the control group was calculated by the equation indicated in EXAMPLE 4. As a result, it was demonstrated that the compounds of the present invention reduced β-lipoproteins, free fatty acids, and triglycerides in the genetically diabetic mice. (Table 9).

TABLE 9

Antihyperlipidemic activities in genetically diabetic mice

| | Reduction Rate (%) | | |
| --- | --- | --- | --- |
| Compound No. | β-lipoproteins | Free Fatty Acids | Triglycerides |
| 1 | 51 | 39 | 69 |
| 3 | 65 | 58 | 85 |

TABLE 9-continued

Antihyperlipidemic activities in genetically diabetic mice

| | Reduction Rate (%) | | |
| --- | --- | --- | --- |
| Compound No. | β-lipoproteins | Free Fatty Acids | Triglycerides |
| 13 | 65 | 38 | 70 |
| 21 | 38 | 25 | 41 |
| 22 | 56 | 41 | 65 |

At a dose of 150 mg/kg p.o.

EXAMPLE 7

Hypotriglyceridemic Activity in Fructose-Induced Hyperlipidemic Rats

The compounds were tested for a hypotriglyceridemic activity in fructose-induced hyperlipidemic rats in accordance with the method described in Nippon Yakurigaku Zasshi, 92 (3), 175–180 (1988). Sprague Dawley rats were grouped by the ranking method of body weight. Then, instead of drinking water, rats were given 75% fructose aqueous ad libitum for one week, thereby, resulting in the state of hypertriglyceridemia. The compounds of the present invention, suspended in 3% Arabic gum aqueous solution, and a dose of 30 mg/kg was orally administrated once daily for 7 days during the fructose-loading period. The control group of rats were given 3% Arabic gum aqueous solution only. Two hours later of the final administration, the rats were bled from the abdominal aorta to measure serum triglycerides and total cholesterol. The results obtained are shown in Table 10. The reduction rate (%) of each measurement compared to the control groups was calculated according to the equation indicated in EXAMPLE 4. These results have demonstrated that the compounds of the present invention have the activity to lower serum triglycerides in hyperlipidemic rats.

TABLE 10

The hypotriglyceridemic activity in fructose induced hyperlipidemic rats

| Compound No. | Reduction in Serum Triglyceride (%) | Compound No. | Reduction in Serum Triglyceride (%) |
| --- | --- | --- | --- |
| 1 | 47 | 20 | 54 |
| 2 | 67 | 21 | 48 |
| 3 | 64 | 22 | 65 |
| 4 | 42 | 26 | 46 |
| 6 | 84 | 28 | 36 |
| 7 | 60 | 32 | 47 |
| 8 | 47 | 34 | 71 |
| 9 | 49 | 37 | 41 |
| 10 | 39 | 39 | 57 |
| 11 | 62 | 40 | 42 |
| 12 | 59 | 43 | 67 |
| 13 | 55 | 45 | 43 |
| 14 | 36 | 47 | 69 |
| 15 | 47 | 49 | 39 |
| 16 | 54 | 51 | 67 |
| 17 | 37 | 52 | 44 |
| 19 | 38 | | |

At a dose of 30 mg/kg p.o.

EXAMPLE 8

Lipid Lowering Effects in High Cholesterol-Fed Hamsters

According to the method described in Jpn Pharmacol Ther, 23 (suppl 4), s1047–1053 (1995), male Syrian hamstars were fed for 3 weeks with 1% cholesterol 10% coconut oil (W/W) supplemented diet, and thereby, became to be hypercholesterolemia models. Prior to administration of the compounds, under ether anesthesia, the hamsters were bled from the orbital vein for measurement of serum total cholesterol. They were grouped in the manner by which the respective groups had almost equal serum total cholesterol levels. The normal group of hamsters were fed ordinary diet. Thereafter, the compound 1 and bezafibrate were orally administered once daily at doses of 15 (for only compound 1), 30, 60 and 120 mg/kg for 7 days. Even during the treatment period, cholesterol loading was continued. Four hours later of the final administration, the hamsters were bled by cardiac puncture. The total cholesterol and triglycerides in the serum obtained were measured by the enzymatic method. The results are shown in Table 11 (the negative values mean elevation rates.)

These results demonstrate that the compounds of the present invention have the activity to lower serum cholesterol and triglycerides serums more efficiently than bezafibrate.

TABLE 11

Effect of the compound 1 and bezafibrate on serum lipid levels in high cholesterol-fed hamsters

| Compound | Bezafibrate | | Compound 1 | |
| --- | --- | --- | --- | --- |
| | Reduction Rate (%)* | | | |
| Activity Dose | Total cholesterol | Triglyceride | Total cholesterol | Triglyceride |
| 15 mg/kg | — | — | 26 | 60 |
| 30 mg/kg | −5 | −21 | 25 | 62 |
| 60 mg/kg | −0 | −18 | 29 | 69 |
| 120 mg/kg | 20 | 16 | 41 | 80 |

*The negative values mean elevation rate.

EXAMPLE 9

Lipid Lowering Effects in High Cholesterol-Fed Hamsters

The actions of the compounds of the present invention at a dose of 15 mg/kg were measured in the same method as described in EXAMPLE 8. The results are shown in Table 12.

TABLE 12

Hypolipidemic effects in high cholesterol-fed hamsters

| | Reduction Rate (%) | |
| --- | --- | --- |
| Compound No. | Total cholesterol | Triglyceride |
| 2 | 27 | 57 |
| 3 | 16 | 17 |
| 7 | 18 | 12 |
| 9 | 15 | 15 |
| 14 | 11 | 24 |
| 15 | 32 | 61 |

At a dose of 15 mg/kg p.o.

EXAMPLE 10

Acute Toxicity Tests with Single Dosing in Mice

The compounds (the compound 1 and 10) of the present invention were singly orally administered to each mouse at a dose of 2000 mg/kg. Then, the mice were observed for 2 weeks. The result was that all 3 mice given the respective compounds survived.

EXAMPLE 11

Mutagenesis Tests

In order to examine mutagenecity of the compound 1, the reverse mutation test was conducted with use of *Salmonella typhimurium* TA100 and TA98.

In the group of the compound 1 treatment, neither of the strains [in the direct method (−s9mix) and also in the metabolically activated method (+s9mix)] did not give rise to an increased number of reversely mutated colonies, therefore, the compound 1 was determined to be non-mutagenic.

As mentioned above, 2-(N-cyanoimino)thiazolidin-4-one derivatives, solvates, and pharmaceutically acceptable salts thereof, provided by the present invention, are useful as therapeutic agents for diabetes, especially as therapeutic agents for the diabetes patients with accompanying complications related to hyperlipidemia such as hypertriglyceridemia and hypercholesterolemia.

What is claimed is:

1. A method for the treatment of diabetes comprising administering to a patient in need thereof a therapeutically effective amount of a pharmaceutical composition comprising a 2-(N-cyanoimino)thiazolidin-4-one derivative represented by the following formula I, or a solvate or a pharmaceutically acceptable salt thereof, as an active ingredient, and a pharmaceutically acceptable carrier:

Formula I

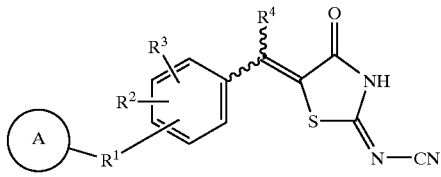

wherein ring A represents a benzene ring, a condensed ring, or a heterocyclic ring, each of which may be substituted by one or more substituents selected from a straight or branched $C_1$–$C_4$ alkyl group, a haloalkyl group, a halogen atom or —$OR^5$, $R^1$ represents a single bond, an oxygen atom, a sulfur atom, a methyne group, a straight or branched $C_1$–$C_4$ alkylene or alkenylene group optionally substituted by a phenyl group, $R^6$—X, X—$R^6$, X—$R^6$—X, $R^6$—X—$R^6$, —C(=O)—$NR^7$— or —$NR^7$—C(=O)—, $R^2$ and $R^3$ are the same or different and each represents a hydrogen atom, a $C_1$–$C_4$ alkyl group, —$OR^8$ or a halogen atom, $R^4$ represents a hydrogen atom or a $C_1$–$C_4$ alkyl group, $R^5$ represents a hydrogen atom or a $C_1$–$C_4$ alkyl group, $R^6$ represents a straight or branched $C_1$–$C_4$ alkylene or alkenylene group, $R^7$ represents a hydrogen atom or a $C_1$–$C_4$ alkyl group, $R^8$ represents a hydrogen atom, a $C_1$–$C_4$ alkyl group or an aralkyl group, X represents an oxygen atom or a sulfur atom, and the configuration of the exocyclic methylene group at 5-position of the thiazolidine ring includes both E- and Z-configuration.

2. The method according to claim 1, wherein ring A represents a benzene ring which may be substituted by one or more substituents selected from a straight or branched $C_1$–$C_4$ alkyl group, a haloalkyl group, a halogen atom or —$OR^5$, $R^5$ represents a hydrogen atom or a $C_1$–$C_4$ alkyl group.

3. The method according to claim 1, which wherein the composition is selected from:

2-(N-Cyanoimino)-5-[(E)-4-styrylbenzylidene]thiazolidin-4-one;

2-(N-Cyanoimino)-5-[(E)-4-(α-methylstyryl)benzylidene]thiazolidin-4-one;

2-(N-Cyanoimino)-5-[4-(benzyloxymethyl)benzylidene]thiazolidin-4-one;

2-(N-Cyanoimino)-5-[(E)-4-(β-methylstyryl)benzylidene]thiazolidin-4-one;

2-(N-Cyanoimino)-5-[4-(3-phenylpropoxy)benzylidene]thiazolidin-4-one;

2-(N-Cyanoimino)-5-[4-(4-chlorophenoxy)benzylidene]thiazolidin-4-one;

2-(N-Cyanoimino)-5-(4-phenylthiobenzylidene)thiazolidin-4-one;

2-(N-Cyanoimino)-5-[(E)-4-(2-fluorostyryl)benzylidene]thiazolidin-4-one;

2-(N-Cyanoimino)-5-[4-(2,5-dimethylphenoxy)benzylidene]thiazolidin-4-one;

2-(N-Cyanoimino)-5-(4-phenethyloxybenzylidene)thiazolidin-4-one;

2-(N-Cyanoimino)-5-[4-(2-phenylpropoxy)benzylidene]thiazolidin-4-one;

2-(N-Cyanoimino)-5-(3-phenethyloxybenzylidene)thiazolidin-4-one;

2-(N-Cyanoimino)-5-(4-benzyloxybenzylidene)thiazolidin-4-one;

2-(N-Cyanoimino)-5-[4-(5-chlorobenzofuran-2-yl)benzylidene]thiazolidin-4-one;

2-(N-Cyanoimino)-5-[(E)-4-(4-methoxystyryl)benzylidene]thiazolidin-4-one;

2-(N-Cyanoimino)-5-(3-phenoxybenzylidene)thiazolidin-4-one;

2-(N-Cyanoimino)-5-[4-(1,3-benzodioxol-5-ylmethoxy)benzylidene]thiazolidin-4-one;

2-(N-Cyanoimino)-5-[4-(4-methylbenzyloxy)benzylidene]thiazolidin-4-one;

2-(N-Cyanoimino)-5-[4-(4-chlorobenzyloxy)benzylidene]thiazolidin-4-one;

2-(N-Cyanoimino)-5-[3-methoxy-E)-4-styrylbenzylidene]thiazolidin-4-one;

2-(N-Cyanoimino)-5-(2-phenethyloxybenzylidene)thiazolidin-4-one;

2-(N-Cyanoimino)-5-(4-phenoxybenzylidene)thiazolidin-4-one;

2-(N-Cyanoimino)-5-[3-(benzyloxy)benzylidene]thiazolidin-4-one;

2-(N-Cyanoimino)-5-[4-(benzylthio)benzylidene]thiazolidin-4-one;

2-(N-Cyanoimino)-5-(4-(phenethylbenzylidene)thiazolidin-4-one;

2-(N-Cyanoimino)-5-[4-[2-(4-chlorophenyl)ethoxy]benzylidene]thiazolidin-4-one;

2-(N-Cyanoimino-5-[1-[(E)-4-(4-methoxystyryl)phenyl]ethylidene]thiazolidin-4-one;

2-(N-Cyanoimino)-5-(4-benzyloxy-2,5-dimethylbenzylidene)thiazolidin-4-one;

2-(N-Cyanoimino)-5-[(E)-3-styrylbenzylidene]thiazolidin-4-one;

and a pharmaceutically acceptable carrier.

4. The method according to claim 1, wherein the 2-(N-cyanoimino)thiazolidin-4-one derivative is 2-(N-cyanoimino)-5-[(E)-4-styrylbenzylidene]thiazolidin-4-one.

5. The method according to claim 1, wherein the diabetes is non-insulin dependent diabetes mellitus.

6. The method according to claim 2, wherein the diabetes is non-insulin dependent diabetes mellitus.

7. The method according to claim 3, wherein the diabetes is non-insulin dependent diabetes mellitus.

8. The method according to claim 4, wherein the diabetes is non-insulin dependent diabetes mellitus.

9. The method according to claim 1, which comprises a hypolipidemic and hypoglycemic activity.

10. The method according to claim 2, which comprises a hypolipidemic and hypoglycemic activity.

11. The method according to claim 3, which comprises a hypolipidemic and hypoglycemic activity.

12. The method according to claim 4, which comprises a hypolipidemic and hypoglycemic activity.

13. The method according to claim 9, wherein the hypolipidemic activity is a hypotriglyceridemic activity.

14. The method according to claim 9, wherein the hypolipidemic activity is a hypocholesterolemic activity.

15. The method according to claim 1, which is for the treatment of diabetes patients accompanied with hyperlipidemia.

16. The method according to claim 1, which is for the treatment of diabetes patients accompanied with hypertriglyceridemia.

17. The method according to claim 1, which is for the treatment of diabetes patients accompanied with hypercholesterolemia.

18. The method according to claim 1, which is for the treatment of diabetes patients accompanied with vascular diseases caused by hyperlipidemia.

* * * * *